(12) United States Patent
Kaiser et al.

(10) Patent No.: US 8,926,613 B2
(45) Date of Patent: Jan. 6, 2015

(54) METHOD AND APPARATUS FOR FORMING A BONE HOLE

(75) Inventors: Ryan A. Kaiser, Leesburg, IN (US); Kevin T. Stone, Winona Lake, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 738 days.

(21) Appl. No.: 13/071,563

(22) Filed: Mar. 25, 2011

(65) Prior Publication Data

US 2012/0245585 A1    Sep. 27, 2012

(51) Int. Cl.
A61B 17/16    (2006.01)
A61B 17/17    (2006.01)

(52) U.S. Cl.
CPC ......... *A61B 17/1796* (2013.01); *A61B 17/1631* (2013.01); *A61B 17/1633* (2013.01)
USPC .............. 606/80; 606/96; 606/74; 606/170; 606/172

(58) Field of Classification Search
CPC ........... A61B 17/1613; A61B 17/1633; A61B 17/1631; A61B 17/1796; A61B 17/1617; A61B 17/1662; A61B 17/1675; A61B 17/320016; A61B 17/32002; A61B 17/164; A61B 17/1671
USPC ........... 606/79–85, 96–98, 99, 100, 167–189, 606/300, 74–75, 328–330
See application file for complete search history.

(56) References Cited

U.S. PATENT DOCUMENTS

| | | | |
|---|---|---|---|
| 4,738,255 A | 4/1988 | Goble et al. | |
| 5,423,824 A * | 6/1995 | Akerfeldt et al. | 606/80 |
| 5,817,095 A | 10/1998 | Smith | |
| 5,885,294 A * | 3/1999 | Pedlick et al. | 606/80 |
| 5,935,134 A | 8/1999 | Pedlick et al. | |
| 6,036,695 A | 3/2000 | Smith | |
| 6,041,485 A | 3/2000 | Pedlick et al. | |

(Continued)

FOREIGN PATENT DOCUMENTS

EP     1864617 B1     10/2009
WO  WO-2012134999 A1  10/2012

OTHER PUBLICATIONS

International Search Report and Written Opinion mailed May 23, 2012 for PCT/US2012/030294 claiming benefit of U.S. Appl. No. 13/071563, filed Mar. 25, 2011.

(Continued)

*Primary Examiner* — Eduardo C Robert
*Assistant Examiner* — Marcela I Shirsat
(74) *Attorney, Agent, or Firm* — Harness, Dickey (57) ABSTRACT

A method and tool for creating a location for a fixation device to be secured to a bone. The method includes bringing a bone cutting tool extending along a longitudinal axis into engagement with an outer surface of the bone. The bone cutting tool is rotated about the longitudinal axis while driving it from the outer surface of the bone to a predetermined depth in the bone to form a bore. The bone cutting tool is then continuously rotated at the predetermined depth to establish an enlarged bone pocket at a distal end of the bore. The bone pocket defines a shoulder extending around a circumference between the bone pocket and bore. The bone cutting tool is removed from the bone pocket and bore. The fixation device is then inserted into the bone pocket through the bore, where it is seated against the bone pocket shoulder.

19 Claims, 10 Drawing Sheets

(56) References Cited

U.S. PATENT DOCUMENTS

| | | |
|---|---|---|
| 6,790,210 B1 | 9/2004 | Cragg et al. |
| 7,601,165 B2 | 10/2009 | Stone |
| 7,658,751 B2 | 2/2010 | Stone et al. |
| 7,749,250 B2 | 7/2010 | Stone et al. |
| 7,857,830 B2 | 12/2010 | Stone et al. |
| 7,905,903 B2 | 3/2011 | Stone et al. |
| 7,905,904 B2 | 3/2011 | Stone et al. |
| 7,909,851 B2 | 3/2011 | Stone et al. |
| 8,088,130 B2 | 1/2012 | Kaiser et al. |
| 8,118,836 B2 | 2/2012 | Denham et al. |
| 8,128,658 B2 | 3/2012 | Kaiser et al. |
| 8,137,382 B2 | 3/2012 | Denham et al. |
| 2003/0220646 A1 | 11/2003 | Thelen et al. |
| 2006/0190042 A1 | 8/2006 | Stone et al. |
| 2006/0195106 A1* | 8/2006 | Jones et al. .............. 606/79 |
| 2008/0255613 A1 | 10/2008 | Kaiser et al. |
| 2008/0319478 A1 | 12/2008 | Foerster et al. |
| 2010/0204700 A1 | 8/2010 | Falahee |
| 2011/0098727 A1 | 4/2011 | Kaiser et al. |
| 2012/0095470 A1 | 4/2012 | Kaiser et al. |

OTHER PUBLICATIONS

International Preliminary Report on Patentability mailed Oct. 10, 2013 for PCT/US2012/030294 which claims benefit of U.S. Appl. No. 13/071,563 filed Mar. 25, 2011.

\* cited by examiner

METHOD AND APPARATUS FOR FORMING A BONE HOLE

FIELD

The present disclosure relates generally to tissue fixation; and relates particularly to an apparatus for forming a bone pocket in a bone.

BACKGROUND

This section provides background information related to the present disclosure which is not necessarily prior art.

In an anatomy, such as a human anatomy, various soft tissue portions are interconnected with various bony portions. For example, a tendon may interconnect a selected muscle group with a selected portion of the anatomy. Similarly, a ligament may interconnect two bony portions. For example, the anterior cruciate ligament (ACL) interconnects a portion of the tibia with a portion of the femur. Although natural and healthy ligaments, tendons, and other selected soft tissues are generally able to support the various portions of the anatomy, injury, age, or other circumstances may cause the weakening or breaking of these various soft tissue portions. In particular, injury or disease may weaken various soft tissue portions, requiring the tissue to be reconnected or replaced with various autografts or xenografts. These various materials may be interconnected with selected portions of the anatomy using soft or flexible suture anchors implanted within a bore formed in the bone.

SUMMARY

This section provides a general summary of the disclosure, and is not a comprehensive disclosure of its full scope or all of its features.

In one form, the present disclosure provides a method for attaching a fixation device to a bone. The method can include bringing a bone cutting tool that extends along a longitudinal axis into engagement with an outer surface of the bone. The method can also include rotating the bone cutting tool about the longitudinal axis while driving the bone cutting tool from the outer surface of the bone to a predetermined depth in the bone to form a bore. The method can include continuously rotating the bone cutting tool at the predetermined depth to establish an enlarged bone pocket at a distal end of the bore. The bone pocket can define a shoulder extending around a circumference between the bone pocket and the bore. The bone cutting tool can then be removed from the bone pocket and the bore. The fixation device can then be inserted into the bone pocket through the bore, where it can be seated against the shoulder of the bone pocket.

In another form, the present disclosure provides a method for attaching a fixation device to a bone. The method can include bringing a bone cutting tool having a helical flute into engagement with an outer surface of the bone. The method can also include rotating the bone cutting tool about a longitudinal axis to form a first bore having a helical flute groove extending from the outer surface of the bone to a depth within the bone. The method can include continuously rotating the bone cutting tool at the depth to establish a second bore having a shoulder and a continuous sidewall. The shoulder can extend around a circumference between the second bore and the first bore. The bone cutting tool can then be aligned with the first bore before be drawn out of the second and first bores. The fixation device can then be inserted into the second bore through the first bore, where it can be positioned against the shoulder of the second bore.

In yet another form, the present disclosure provides a bone cutting tool including a body portion extending from a proximal end to a distal end along a central longitudinal axis. The body portion can include proximal shaft portion having a first diameter and a distal drill portion having a second diameter greater than the first diameter. A tapered drill end can extend from the distal end of the body portion and be adapted to engage a bone. A sleeve member can define an elongated bore adapted to rotatably receive the proximal shaft portion. The sleeve member can be movable between a first location and a second location.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

The following description of various embodiments is merely exemplary in nature and is not intended to limit the present disclosure, its application, or uses. It should be understood that throughout the drawings, corresponding reference numerals indicate like or corresponding parts and features. With reference to FIGS. 1-16, various methods and apparatuses are disclosed according to the present teachings for providing a bone socket for receipt of a soft suture anchor. However, the various apparatuses and methods may also be used for a plurality of procedures. For example, the various instruments may be used to affix or hold a hamstring, Achilles tendon allograft, other soft tissue, or any other appropriate portion. In addition, although various embodiments may illustrate soft anchor fixation, it will be understood that any securing member may be situated in a bone bore formed by the various instruments. Therefore, it will be understood that the following discussions are not intended to limit the scope of the present teachings or claims herein.

Referring now to FIGS. 1-4 of the drawings, a bone cutting tool is generally indicated by reference number 10. Bone cutting tool 10 can be any tool operable for forming an open- or closed-end bore having a shoulder in a bone 12 for receipt of a tissue-anchoring device (e.g., a tap as shown in FIGS. 1-4 or a drill as shown in FIGS. 5-15). An exemplary anchoring device is a soft or flexible suture anchor 14, such as the suture-anchoring device described in co-pending U.S. patent application Ser. Nos. 12/915,962 and 11/935,681, both incorporated herein by reference. Soft suture anchor 14 is operable for securing a tissue 16 (e.g., xenograft, allograft, or bone) to bone 12 (see FIG. 4). Soft suture anchor 14 is illustrated to include a bone fixation element 18 and a tissue fixation element 20 interconnected through a suture 22, as will be described below. Those skilled in the art will understand that soft suture anchor 14 may be formed from a non-resorbable material or a resorbable material of the types that are well known in the art so as to permit bone fixation element 18, tissue fixation element 20, and suture 22 to bioabsorb over a selected time span, such as within the time span of the healing process.

Figure 1:
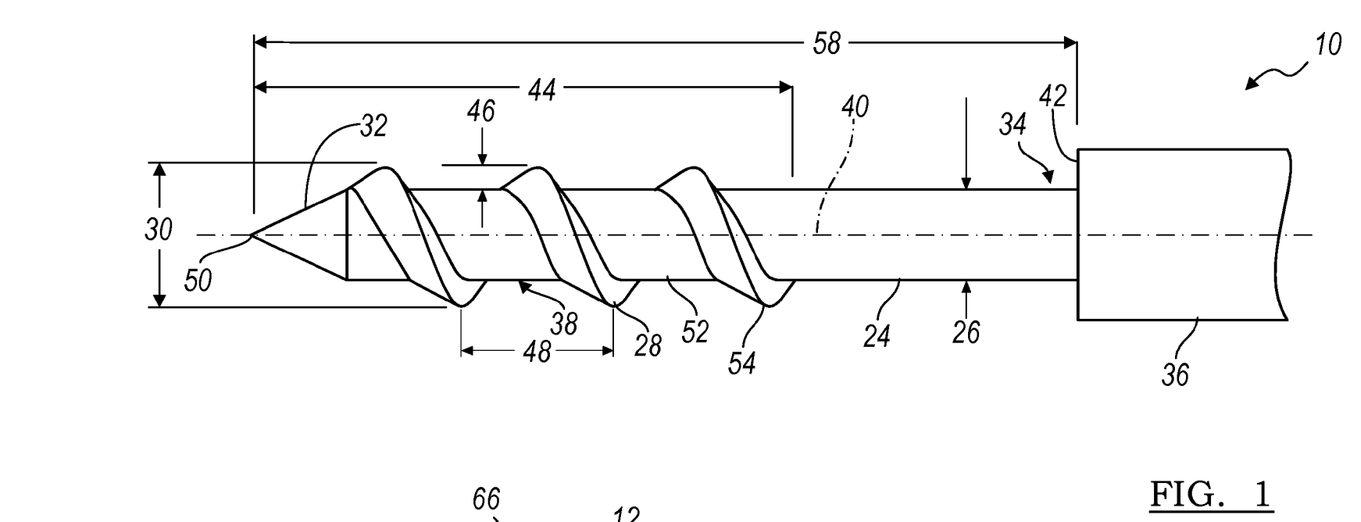
FIG. 1 is a side view of a bone cutting device constructed in accordance with the teachings of the present disclosure.

With particular reference to FIG. 1, bone cutting tool 10 is shown to include an elongated body or shaft portion 24 having a first diameter 26, at least one distally positioned helical cutting tooth or flute 28 defining a second diameter 30, and a distal tapered end 32. Body portion 24 includes a proximal end 34 configured for receipt by a driving device 36 (e.g., a handle or a chuck of a power drill) and a distal end 38 forming helical cutting tooth 28 and terminating at tapered end 32. Helical cutting tooth 28 can be formed by machining the distal end 38 or otherwise connecting the tooth 28 to the distal end 38. Body portion 24 extends along a longitudinal axis 40 and is configured so as to provide first diameter 26 as a constant over its length. Alternately, body portion 24 may have a varied diameter so as to form an integral shoulder portion (not shown) at the proximal end 34 for receiving an external driving means (e.g., driving device 36). Driving device 36 has a larger size than that of first diameter 26, thereby forming a stop 42 therebetween that can act as a stop or depth limiter.

Helical cutting tooth 28 is coupled to body portion 24 and may extend therefrom by a predetermined length 44, width 46, and pitch 48. For example, helical cutting tooth 28 may extend by length 44 from a distal most tip 50 of tapered end 32 towards proximal end 34. Width 46 may correspond to a distance between an outer surface 52 of body portion 24 and an apex 54 of tooth 28. Accordingly, the second diameter 30 of bone cutting tool 10 may be larger than the first diameter 26 of body portion 24. Notably, predetermined length 44, width 46, and pitch 48 can be varied to provide an appropriately dimensioned bone pocket 56 for receipt of soft suture anchor 14, to accommodate varying bone constructs and densities. Additionally, body portion 24 may have a length 58 extending from distal most tip 50 to stop 42 for establishing the location of bone pocket 56 within the bone 12. For example, length 44 may be 5.0 to 15.0 mm, width 46 may be 0.5 to 1.0 mm, pitch 48 may be 2.0 to 4.0 mm, and length 58 may be 10.0 to 20.0 mm.

Figure 2:
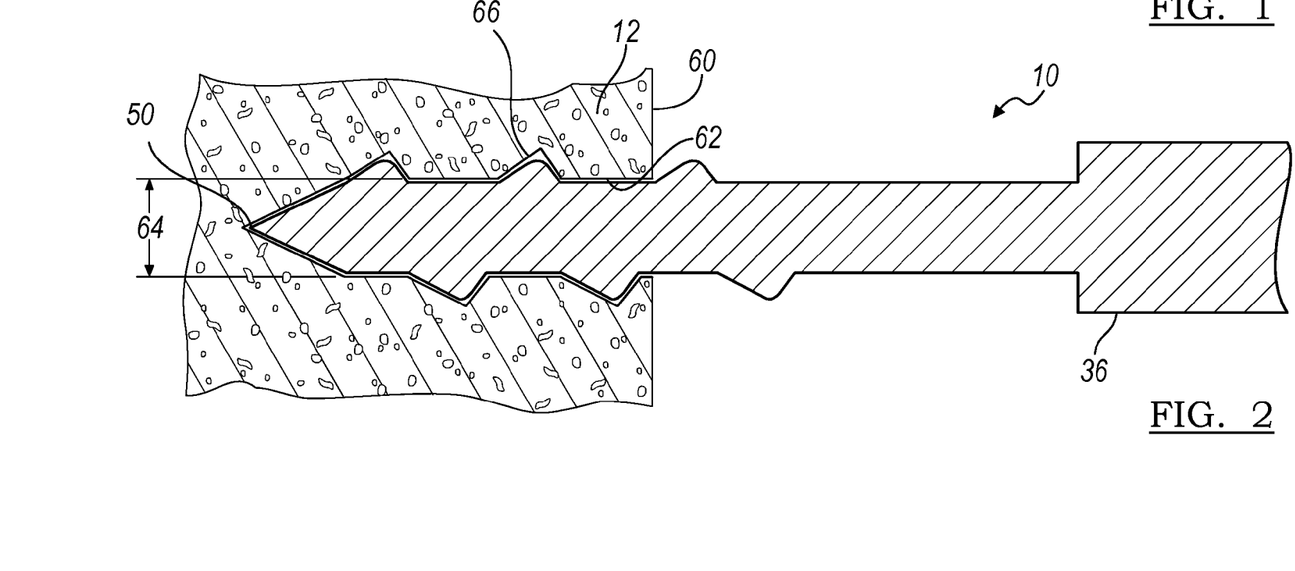
FIG. 2 is a cross-sectional view of the bone cutting device of FIG. 1 in an initial operative position in association with a bone of a body.
Figure 3:
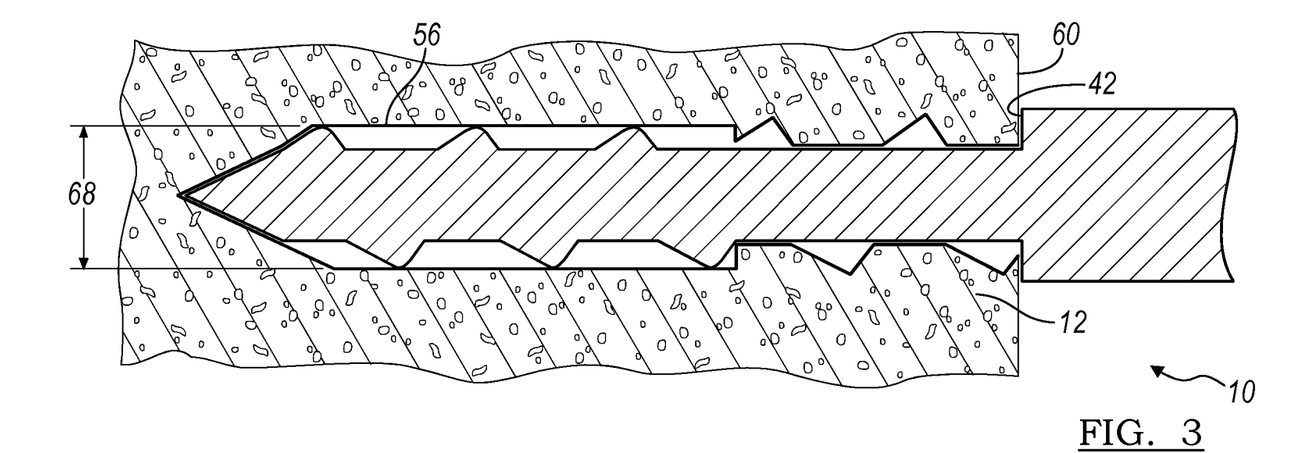
FIG. 3 is a cross-sectional view of the bone cutting device of FIG. 1 in a final operative position in association with the bone of the body.
Figure 4:
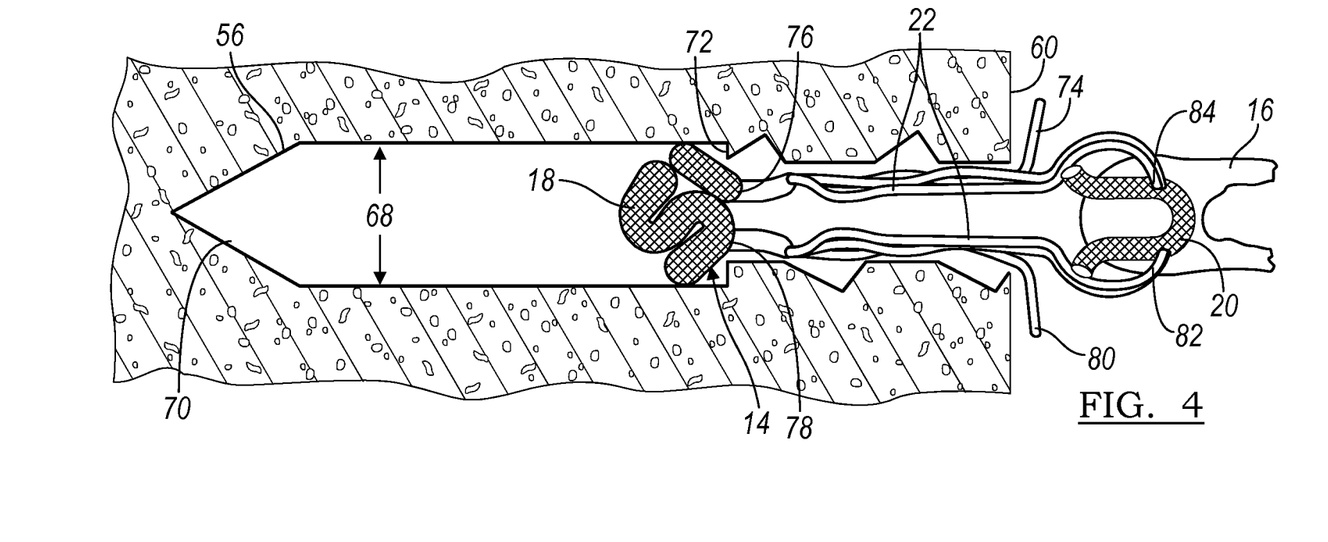
FIG. 4 is a cross-sectional view of a bone socket established by the bone cutting device of FIG. 1 having a soft suture anchor inserted therewith.

Referring now to FIGS. 2-4, the foregoing bone cutting tool 10 may be used to form a blind bore, concavity, or hole having a substantially uninterrupted 360° internal shoulder 72 within bone 12. In particular, distal most tip 50 is brought into contact with an outer surface 60 of bone 12. Bone cutting tool 10 is rotated around longitudinal axis 40 by manipulation of driving device 36. Bone cutting tool 10 gradually moves or is driven into and through outer surface 60 of bone 12 by the cutting action of helical cutting tooth 28. Helical cutting tooth 28 pulls bone cutting tool 10 into bone 12 in a corkscrew motion designed to draw the bone cutting tool 10 inwardly. It should be understood that bone cutting tool 10 is designed to penetrate cortical bone and establish bone pocket 56 within either cancellous or cortical bone. It should be noted, however, that bone cutting tool 10 may be sized to provide bone pocket 56 completely within cortical bone. In either case, bone cutting tool 10 produces a hole, concavity, or blind bore 62 within bone 12 having an inner diameter 64 that corresponds to first diameter 26. Bone cutting tool 10 proceeds inwardly of bone 12 until stop 42 meets outer surface 60.

Helical cutting tooth 28 establishes a single helical groove 66 in cylindrical bore 62 during inward rotation, as can be seen in FIG. 2. Single helical groove 66 extends from outer surface 60 to the beginning of distal tapered end 32 when the bone cutting tool 10 is at the predetermined desired depth into the bone 12. Without removing bone cutting tool 10 from bore 62, bone cutting tool 10 is then repeatedly or continuously rotated around longitudinal axis 40 by manipulation of driving device 36, so as to mill out bone pocket 56. The continuous rotation bores a portion of bone 12 to a second, inner diameter 68 about equivalent to the distance from opposing-facing apices 54 of tooth 28, as can be seen in FIG. 3. In other words, the bone cutting tool 10 is continuously rotated at the predetermined depth to establish the enlarged bone pocket 56 at the distal end of the bore 62. The inner diameter 68 of the bone pocket 56 is diametrically greater than the size of the inner diameter 64 of the bore 62. Bone cutting tool 10 is then slowly backed out of bone 12 leaving bore 62 terminating at bone pocket 56. In order to back bone cutting tool 10 out of bone 12, helical cutting tooth 28 may be brought back into engagement with the helical groove 66 in the bore 62. This may be achieved by putting slight back pressure on driving device 36, so as to allow helical cutting tooth 28 to catch on the single helical groove 66 in the cylindrical bore 62. The bone cutting tool 10 is then rotated around the longitudinal axis 40, but in reverse. Alternatively, a second helix form may be established during outward rotation of bone cutting tool 10 (not shown).

As can be seen in FIG. 4, bone pocket 56 includes a tapered cone 70 corresponding in shape and size to distal most tip 50, inner diameter 68 corresponding to the second diameter 30, and a substantially uninterrupted 360° shoulder 72 defined between the bore 62 and the bone pocket 56. Tapered cone 70 may terminate at a location within the bone 12 corresponding in length to the distance between stop 42 and distal most tip 50, or in other words length 58 (e.g., 15.0 mm). Shoulder 72 may be located within the bone 12 at a distance from outer surface 60 at a dimension equal to the difference between length 58 and length 44 (e.g., 5.0 mm).

Bone pocket 56 is sized to receive a deformable fixation device, such as soft suture anchor 14. It should be understood that while one exemplary soft suture anchor 14 is described herein, other anchoring devices are contemplated. For example, soft anchors having a single suture extending therethrough or rigid anchors, may be used. Soft suture anchor 14 can be preformed to include a looped configuration having at least one looped suture 22 and a pair of flexible anchors or bone fixation element 18 and tissue fixation element 20, as described in co-pending U.S. patent application Ser. No. 12/915,962, incorporated herein by reference. In one example as shown herein, looped suture 22 may traverse a path from one end of bone fixation element 18 to the other end thereof. Soft suture anchor 14 can be formed by passing a first suture end 74 through a first aperture 76 in bone fixation element 18 and out a second aperture 78 in bone fixation element 18. A second end 80 is then passed in through second aperture 78 in bone fixation element 18 and out first aperture 76 in bone fixation element 18. Passing ends 74, 80 through apertures 76, 78 can form looped suture 22. Similarly, ends 74, 80 are passed through apertures 82, 84 of tissue fixation element 20.

The soft suture anchor 14 has a first configuration during installation and a second configuration upon applying tension to first and second ends 74, 80. In particular, the configuration of the looped suture 22 can be placed in a desired tension to engage shoulder 72. Tension in looped suture 22 can cause constriction throughout soft suture anchor 14. This constriction can cause soft suture anchor 14 to "automatically" lock in a compressed configuration. Further tension on ends 74, 80 causes tissue 16 to be brought into engagement with outer surface 60 of bone 12. This can fix selected tissue 16 (e.g., a ligament) to bone 12 in which the bone pocket 56 is formed.

With reference now to FIGS. 5-9, an alternative bone cutting tool 100 is shown. Bone cutting tool 100 is also operable for preparing a bone 112 for receipt of a tissue anchoring device, such as soft suture anchor 14, as previously described. Soft suture anchor 14 is not described in conjunction with bone cutting tool 100; however, its insertion within a bone pocket 156 is similar to that described with reference to bone cutting tool 10 and bone pocket 56 as shown in FIG. 4.

Figure 5:
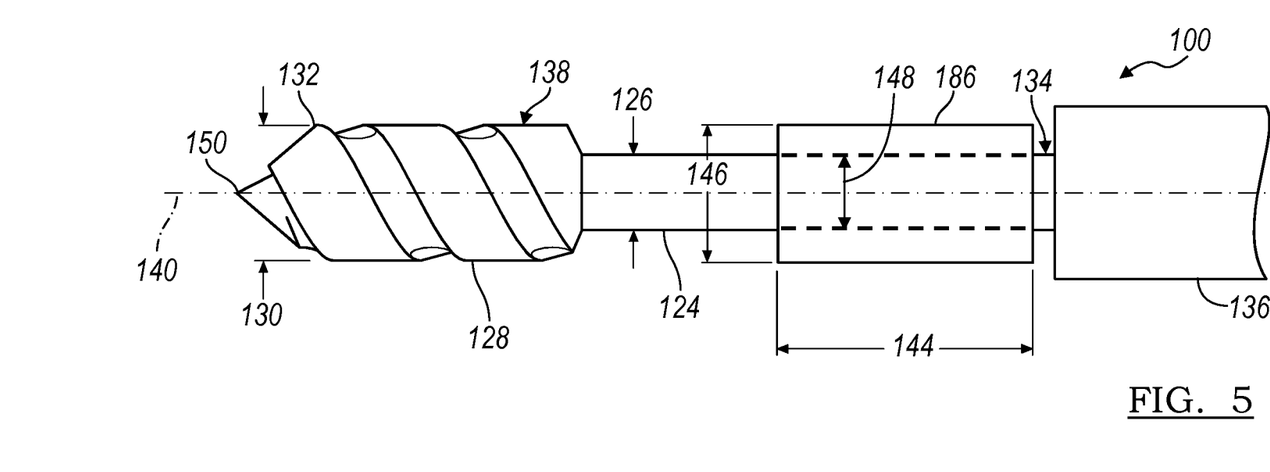
FIG. 5 is a side view of an alternate bone cutting device constructed in accordance with the teachings of the present disclosure.
Figure 6:
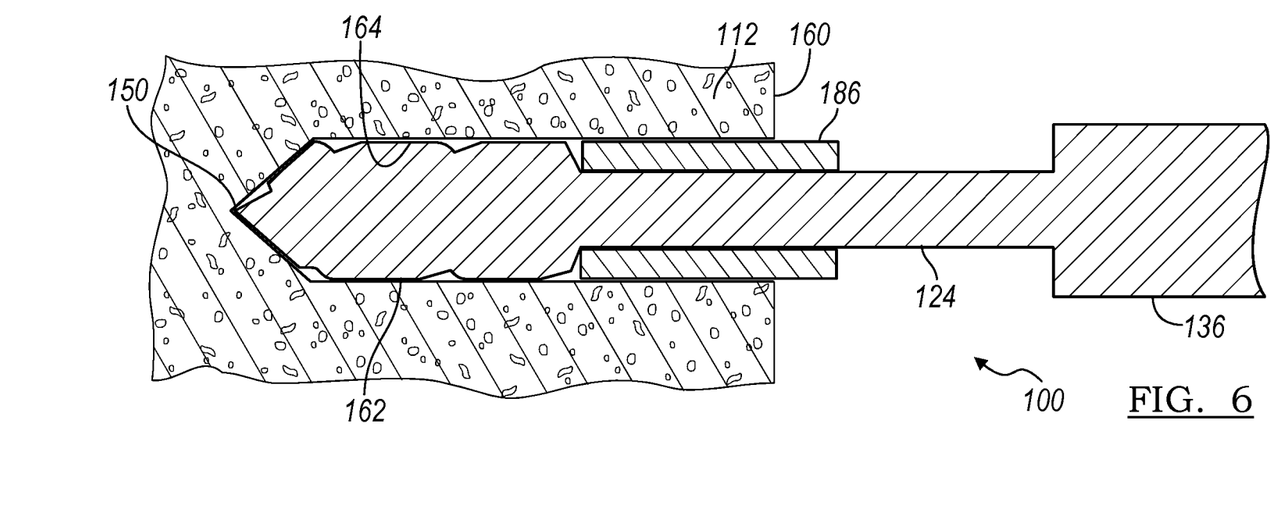
FIG. 6 is a cross-sectional view of the bone cutting device of FIG. 5 in an initial operative position in association with a bone of a body.

With particular reference to FIG. 5, bone cutting tool 100 is shown to include a shaft or body portion 124, a tubular sleeve 186, and a tapered drill end 132. Body portion 124 includes a proximal end 134 configured for receipt of a driving device 136 (e.g., a handle, a chuck of a power drill) and a distal end 138 supporting tapered drill end 132. While body portion 124 is described as receiving driving device 136, it should be understood that distal end 138 may also terminate in an expanded shoulder (not shown) capable of insertion within a chuck (not shown) of the driving device 136. Furthermore, driving device 136 may be an integral piece used as a depth stop and also as a pivot point when maneuvering the drill (see FIG. 8A).

Tapered drill end 132 of bone cutting tool 100 may terminate at a distal most tip 150. Tapered drill end 132 can include cutting teeth or flutes 128 for axial and/or transverse cutting. Tapered drill end 132 may be self-tapping, so as to omit the need for a second, preparatory tool. Body portion 124 is situated along a longitudinal axis 140 and is configured to have a constant shaft diameter 126 over its length. Body portion 124 may be formed from a rigid material (e.g., stainless steel) or may be a more elastic material (e.g., nitinol).

Sleeve 186 may have a predetermined length 144, outer diameter 146, and concentric inner diameter 148 and may be slidingly coupled to body portion 124. Length 144 and outer diameter 146 of sleeve 186 may correspond to a selected depth and width of cut in bone 112, as outer diameter 146 of sleeve 186 is approximately equal to an outer diameter 130 of tapered drill end 132. Notably, predetermined length 144 and outer diameter 146 can be varied to provide an appropriately dimensioned bone pocket 156 for receipt of soft suture anchor 14, to accommodate varying bone constructs and densities. Inner diameter 148 may be slightly larger than shaft diameter 126, so as to allow sleeve 186 to glide over body portion 124 during use. Sleeve 186 may be a rigid material (e.g., stainless steel), so as to provide stiffness to body portion 124 during insertion into bone 112. Sleeve 186 may also work as a centralized cutting guide for bone cutting tool 100 during insertion into bone 112, as will be described in detail below.

Referring now to FIGS. 6-9, the foregoing bone cutting tool 100 may be used to form an undercut or shoulder 172 in bone 112. In particular, distal most tip 150 is brought into contact with an outer surface 160 of bone 112. Bone cutting tool 100 is rotated around longitudinal axis 140 by manipulation of driving device 136. Gradually, bone cutting tool 100 moves into and through outer surface 160 of bone 112 by the cutting action of tapered drill end 132. Bone cutting tool 100 produces a bore 162 within bone 112 having an inner diameter 164 that corresponds to the outer diameter 130 of tapered drill end 132 and outer diameter 146 of sleeve 186. Bone cutting tool 100 advances inwardly of bone 112 until a desired cutting depth is reached.

Figure 7:
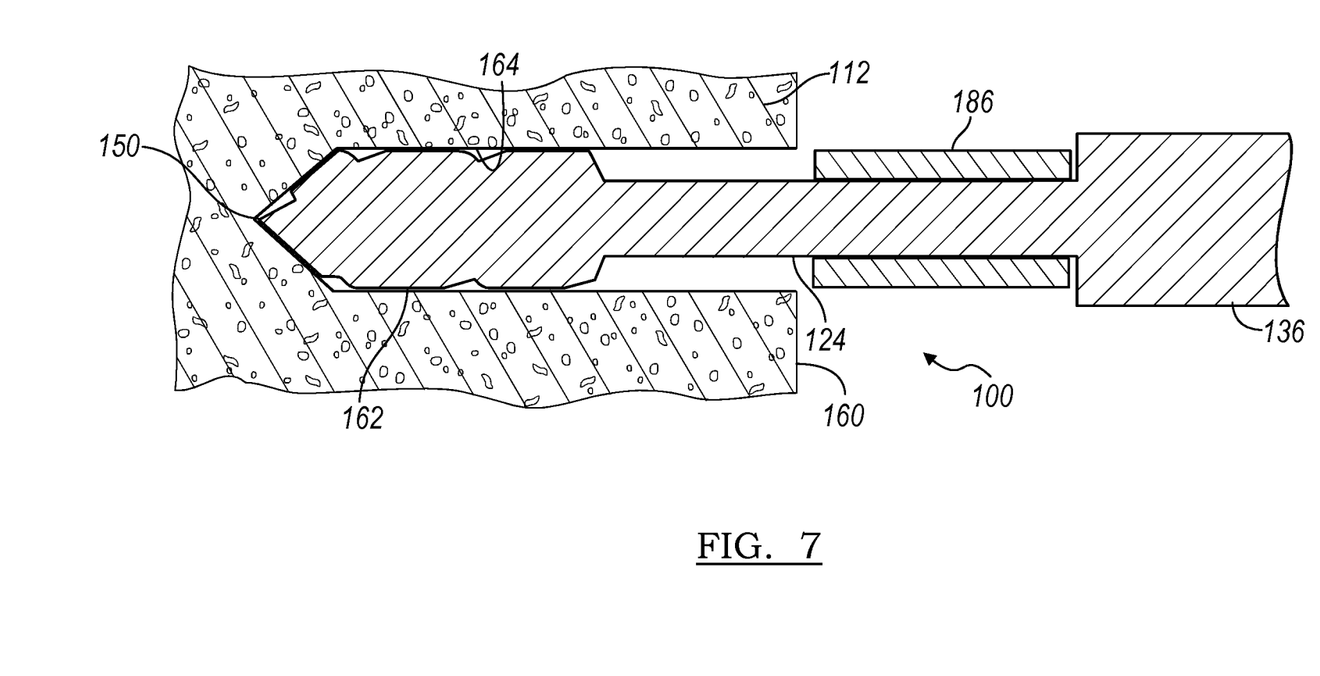
FIG. 7 is a cross-sectional view of the bone cutting device of FIG. 5 in an intermediate operative position in association with the bone of the body.

Sleeve 186 is then retracted from bore 162 within bone 112. Bone cutting tool 100 can then be further rotated by manipulation of driving device 136. As body portion 124 and tapered drill end 132 are no longer supported by sleeve 186, they are allowed to freely move within bore 162. The movement can be either randomized or can be cyclical as performed by a user, but is typically defined as a pivot of the body portion 124 near the entrance to the bore 162. The side or transverse cutting flutes 128 allow cutting of bone 112 transverse to the axis 140.

Figure 8A:
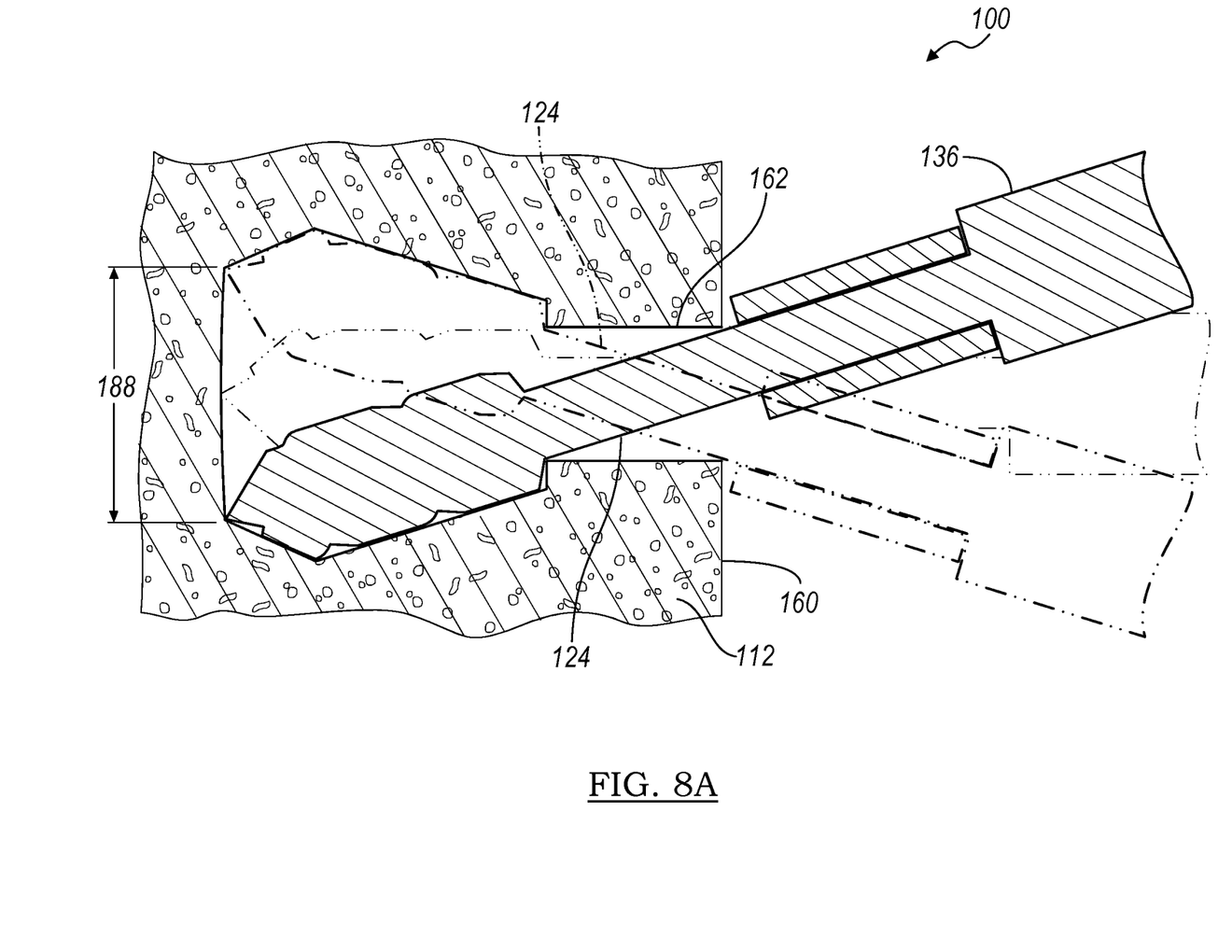
FIG. 8A is a cross-sectional view of the bone cutting device of FIG. 5 in a final operative position in association with the bone of the body and having a rigid body portion.
Figure 8B:
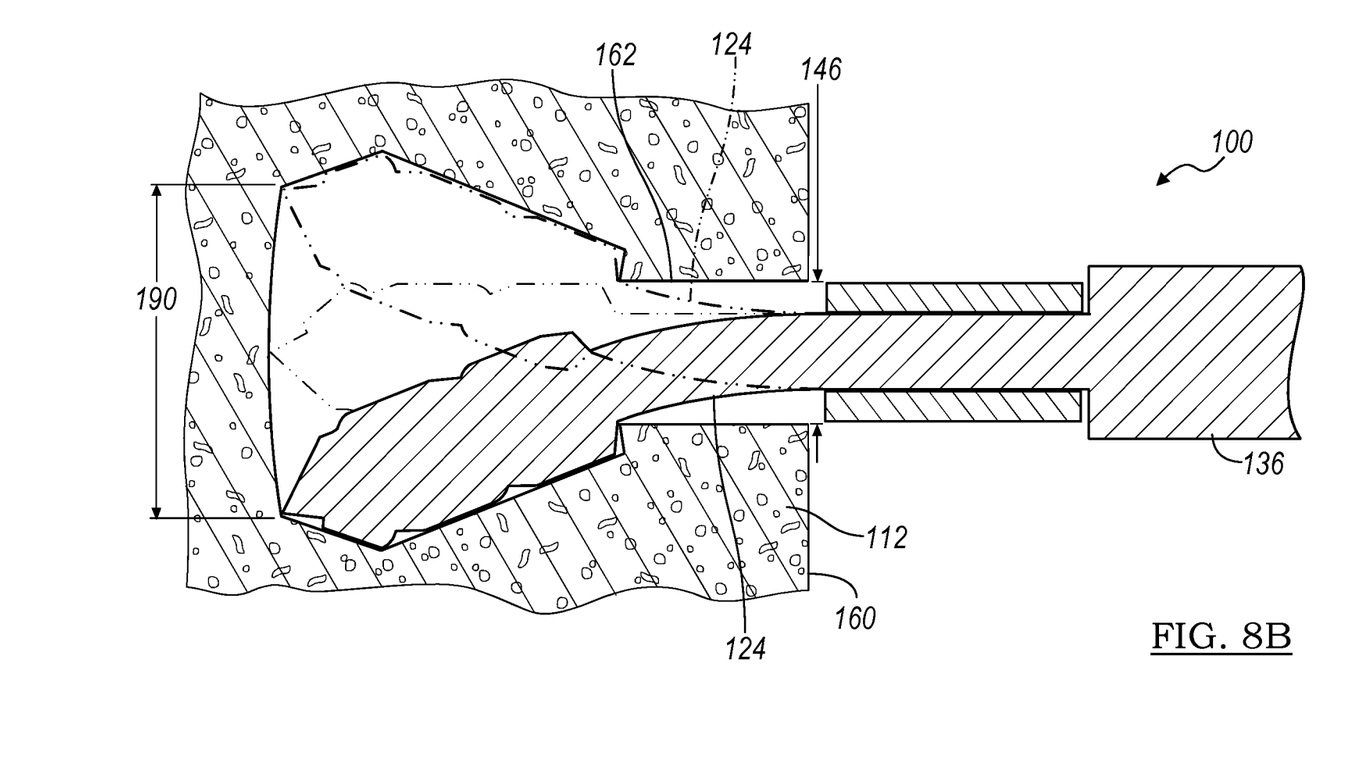
FIG. 8B is a cross-sectional view similar to that of FIG. 8A having a flexible body portion.

It should be understood that when body portion 124 can be formed from an elastic material, the range of tapered drill end 132 may be greater than when body portion 124 is formed from a rigid material. For example, FIG. 8A shows body portion 124 formed from a rigid material, while FIG. 8B shows body portion 124 formed from an elastic material. As can be seen, a diametrical range 188 of tapered drill end 132 in FIG. 8A is smaller than that of a diametrical range 190 of tapered drill end 132 in FIG. 8B. While body portion 124 is described and illustrated as a straight shaft, it should be understood that body portion 124 may also be formed to include a multi-piece pivoting arrangement (e.g., a pivot driver). In this way, body portion 124 may include an elbow (not shown) at a midpoint thereof. The elbow can allow the body portion 124 to flex in a mode similar to that shown in FIG. 8B. Therefore, size of bone pocket 156 is directly related to material and/or configuration of body portion 124. Bone cutting tool 100 may then be oriented with bore 162 and then backed out of bone 112. In this way, all cutting operations are performed without removing bone cutting tool 100 from bore 162.

Figure 9:
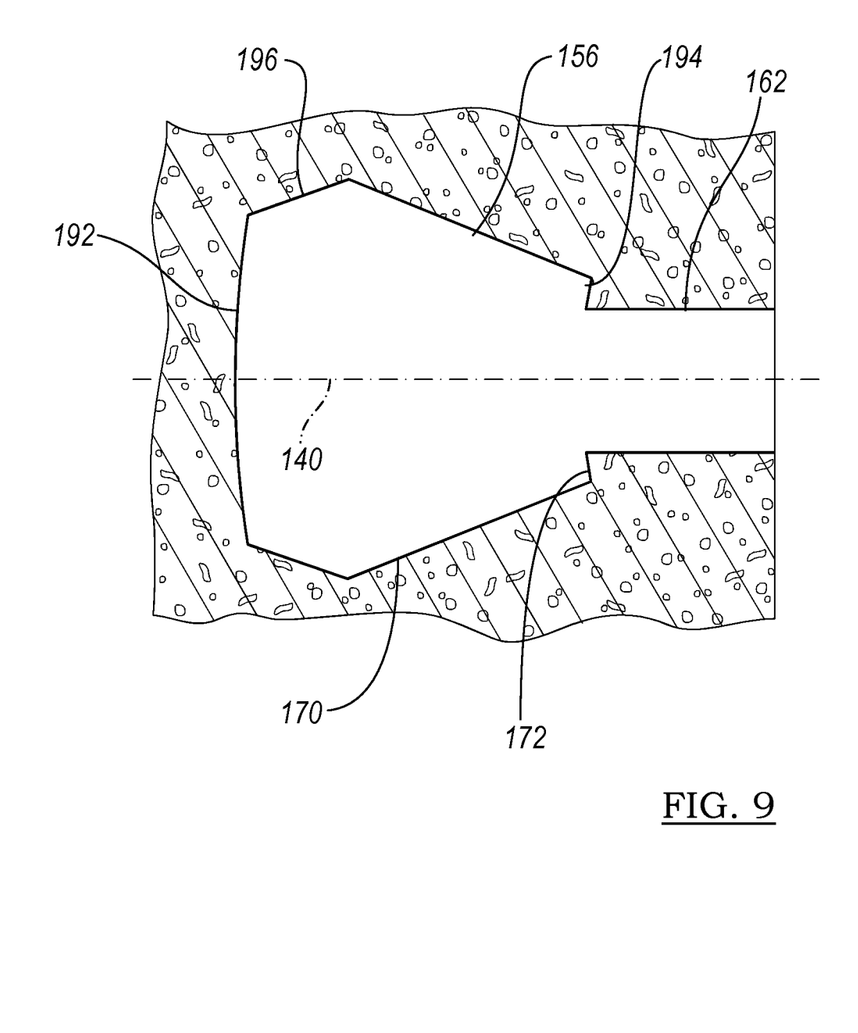
FIG. 9 is a cross-sectional view of a bone socket established by the bone cutting device of FIG. 5.

As can be seen in FIG. 9, bore 162 terminates at bone pocket 156. Bone pocket 156 includes a widened socket 170 including an arc-shaped distal end 192 and a convex shoulder 172 forming a circumferential tooth 194. The arc-shaped distal end 192 corresponds to the path of cutting of the distal most tip 150. The arc-shaped distal end 192 may be adjacent to an angled side 196 corresponding to the profile of the tapered drill end 132. The angled side 196 may extend around a periphery of the arc-shaped distal end 192 and may terminate at the circumferential tooth 194 of the convex shoulder 172. The convex shoulder 172 may extend 360° around the periphery of the bore 162 between the widened socket 170 and the bore 162. While the bone pocket 156 is shown with a symmetrical arrangement, it should be understood that the bone pocket 156 may also have an asymmetrical arrangement dictated by the cyclical movement of the bone cutting tool 100. In either case, however, bone pocket 156 is sized to receive soft suture anchor 14, as previously described. It should be understood that the selection of shaft material may be directly related to the size of the suture anchor to be inserted within the bone pocket 156. For example, the larger size of the bone pocket 156 obtained with a flexible material may be necessary for larger suture anchors.

With reference now to FIGS. 10-16, an alternative bone cutting tool 200 is shown. Bone cutting tool 200 is also operable for preparing a bone 212 for receipt of a tissue anchoring device, such as soft suture anchor 14, as previously described. Soft suture anchor 14 is not described in conjunction with bone cutting tool 200; however, its insertion within a bone pocket 256 is similar to that described with reference to bone cutting tool 10 and bone pocket 56 as shown in FIG. 4.

Figure 10:
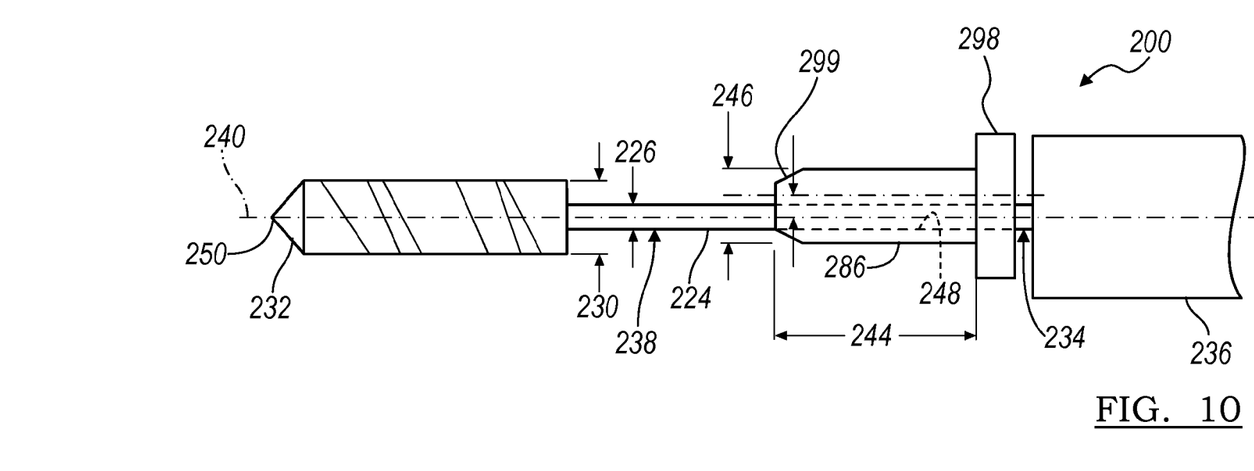
FIG. 10 is a side view of another alternate bone cutting device constructed in accordance with the teachings of the present disclosure.
Figure 11:
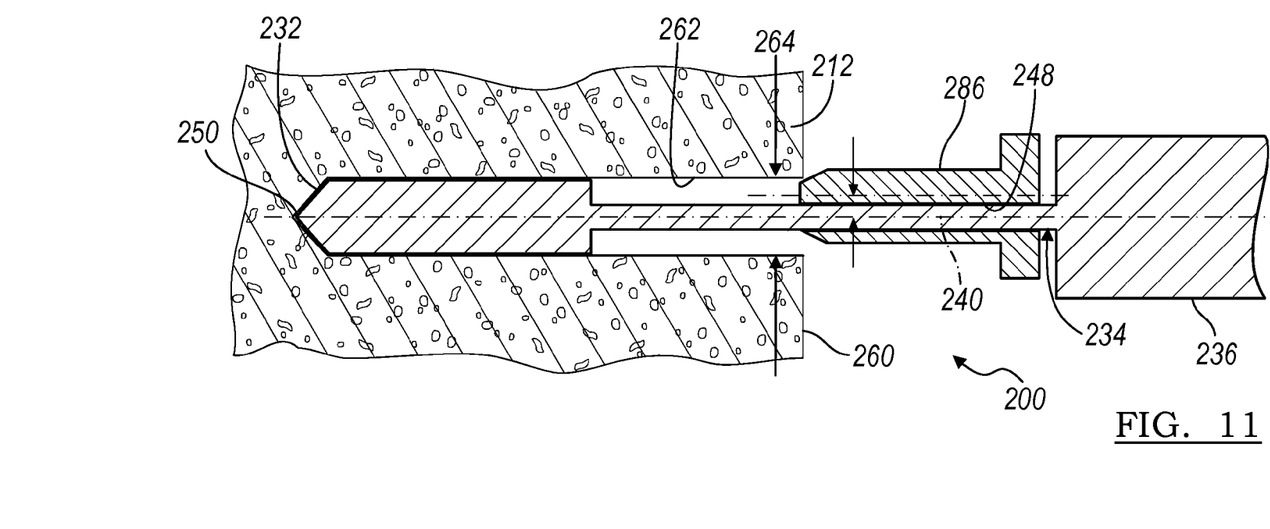
FIG. 11 is a cross-sectional view of the bone cutting device of FIG. 10 in an initial operative position in association with a bone of a body.

With particular reference to FIG. 10, bone cutting tool 200 is shown to include a body portion 224, a sleeve 286, and a tapered drill end 232. Body portion 224 includes a proximal end 234 configured for receipt of a driving device 236 (e.g., a handle, a chuck of a power drill) and a distal end 238 supporting tapered drill end 232. Tapered drill end 232 of bone cutting tool 200 may terminate at a distal most tip 250. Body portion 224 extends along a longitudinal axis 240 and is configured to have a constant shaft diameter 226 over its length. Body portion 224 may be formed from a rigid material (e.g., stainless steel).

Sleeve 286 may have a predetermined length 244 and outer diameter 246. Sleeve 286 may also have a non-concentric or offset inner aperture 248, a flange 298, and a chamfered end 299. Length 244 of sleeve 286 may correspond to a selected depth of cut in bone 212 with flange 298 limiting movement of sleeve 286, as will be described in more detail below. Outer diameter 246 may correspond to an outer diameter 230 of tapered drill end 232. Furthermore, inner aperture 248 may be slightly larger than shaft diameter 226 so as to allow sleeve 286 to glide over body portion 224 during use. As should be understood, diameters 230, 246 and location of offset inner aperture 248 can be varied to provide an appropriately dimensioned bone pocket 256 for receipt of soft suture anchor 14, to accommodate varying bone constructs and densities.

Referring now to FIGS. 11-15, the foregoing bone cutting tool 200 may be used to form an undercut in bone 212 with sleeve 286 working as a guide for cutting bone pocket 256 after insertion to appropriate depth into bone 212. In particular, distal most tip 250 is brought into contact with an outer surface 260 of bone 212, while sleeve 286 is located at a position away from the tapered drill end 232. Bone cutting tool 200 is rotated around longitudinal axis 240 by manipulation of driving device 236. Gradually, bone cutting tool 200 moves into and through outer surface 260 of bone 212 by the cutting action of tapered drill end 232. Bone cutting tool 200 may establish a bore 262 within bone 212 having an inner diameter 264 that corresponds to the outer diameter 230 of tapered drill end 232. Bone cutting tool 200 advances inwardly of bone 212 until an appropriate cutting depth is reached.

Figure 12:
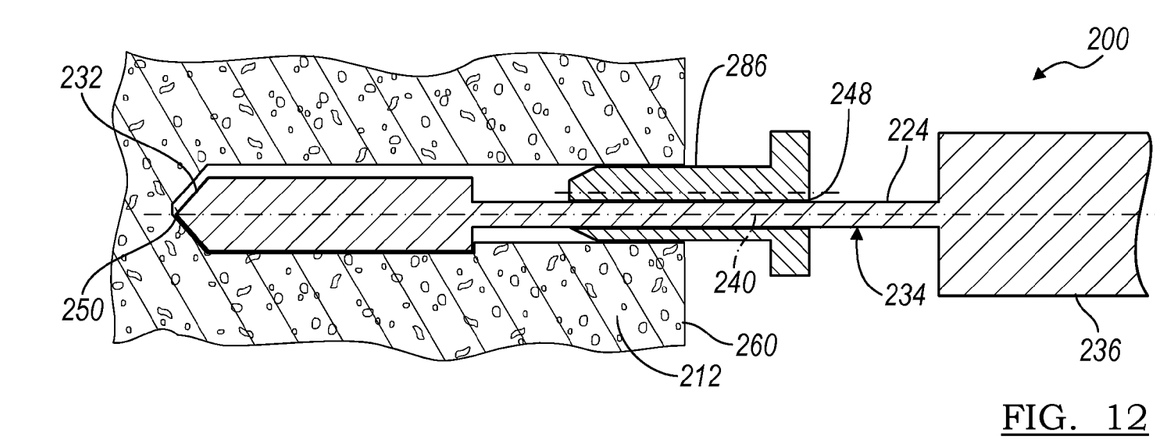
FIG. 12 is a cross-sectional view of the bone cutting device of FIG. 10 incorporating a sleeve in a first intermediate operative position in association with the bone of the body.
Figure 13:
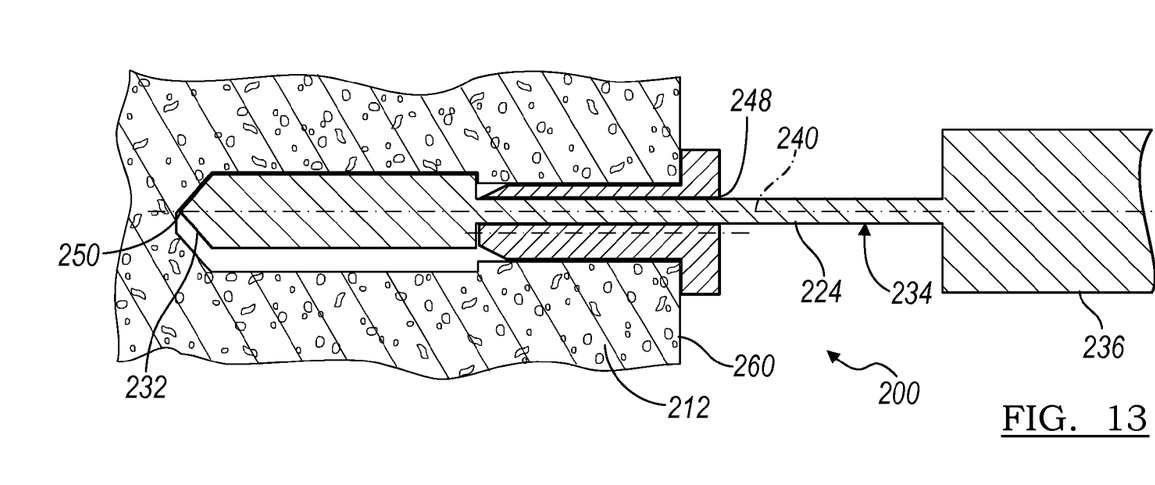
FIG. 13 is a cross-sectional view of the bone cutting device of FIG. 10 incorporating the sleeve in a second intermediate operative position in association with the bone of the body.
Figure 14:
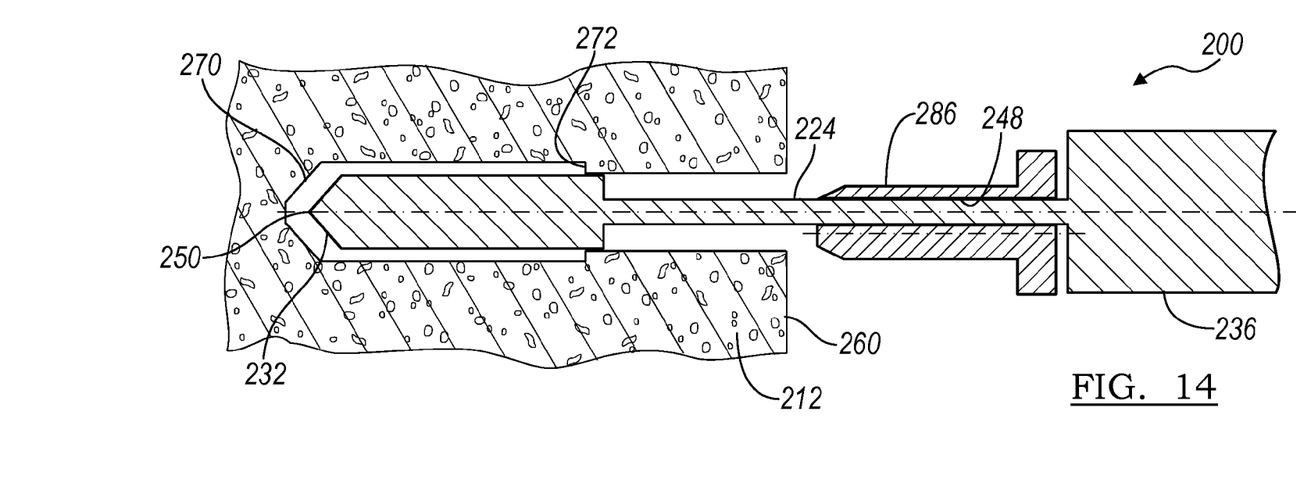
FIG. 14 is a cross-sectional view of the bone cutting device of FIG. 10 in a final operative position in association with the bone of the body.

Chamfered end 299 of sleeve 286 is then inserted into bore 262. Continuous rotation of bone cutting tool 200 by manipulation of driving device 236, while simultaneously applying axial and rotational force to sleeve 286, causes eccentric rotation of tapered drill end 232 allowing the sleeve 286 to be inserted into the bore 262. Movement of sleeve 286 into bore 262 forces body portion 224 and tapered drill end 232 to cut into bore 262 in a spiraled offset manner. Sleeve 286 is prevented from moving further into bone 212 by flange 298. As bone 212 is removed from bore 262, a bone pocket 256 is formed having a 360° shoulder 272 therewith. Each rotation of tapered drill end 232 causes sleeve 286 to more freely move within bore 262. Accordingly, tapered drill end 232 begins to move freely within bore 262, but only to the extent permitted by the dimensional offset of inner aperture 248.

Figure 15:
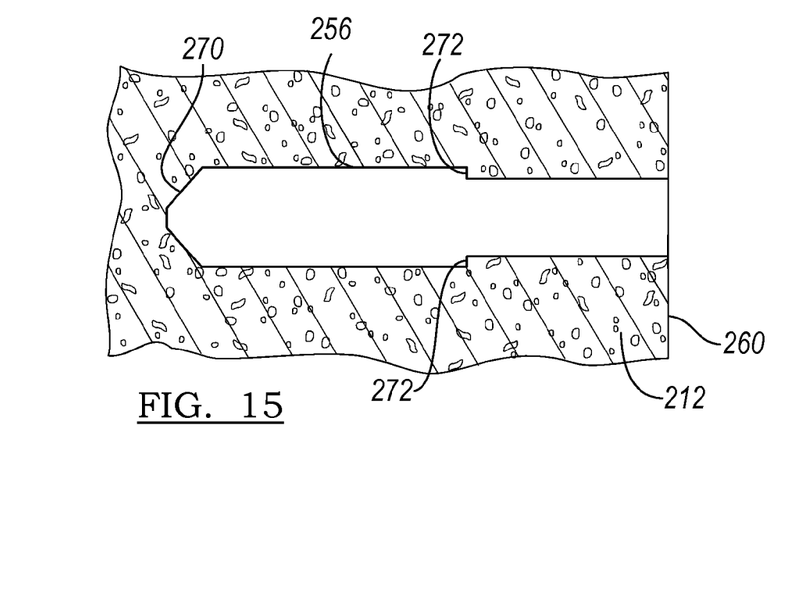
FIG. 15 is a cross-sectional view of a bone socket established by the bone cutting device of FIG. 10 and the sleeve of FIG. 12.

As can be seen in FIG. 15, bone cutting tool 200 is then centered and reversed out of bore 262 and bone 212. Bone pocket 256 includes a widened socket 270 and 360° shoulder 272, corresponding in shape and size to tapered drill end 232. Bone pocket 256 is sized to receive soft suture anchor 14, as previously described.

Figure 16:
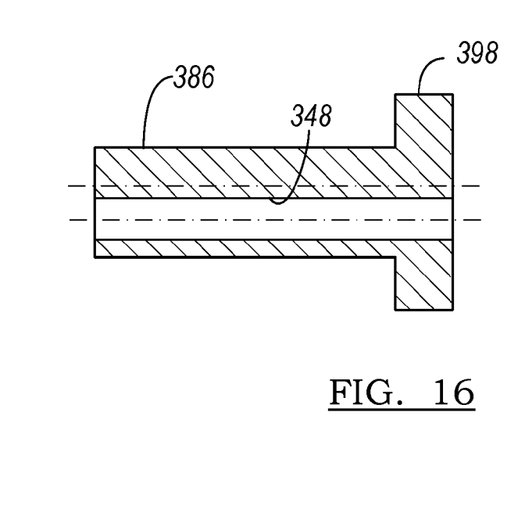
FIG. 16 is a cross-sectional view of an alternate sleeve for use with the bone cutting device of FIG. 10.

With reference now to FIG. 16, an alternate sleeve 386 is shown for attachment to the bone cutting tool 200. Sleeve 386 includes an offset inner aperture 348 and a flange 398, which function as described above. Accordingly, alternative sleeve 386 is similar to the sleeve 286 of FIGS. 10-15, but does not include chamfered end 299. When sleeve 386 is in use, bone cutting tool 200 may be manually angled to allow for insertion of sleeve 386 into bore 262.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for attaching a fixation device to a bone, the method comprising:

bringing a bone cutting tool into engagement with an outer surface of the bone, the cutting tool having a body portion and a drilling portion, the body portion having a constant first diameter, a proximal end and a distal end, the drilling portion having a second diameter larger than the first diameter and terminating at a drill tip, the body portion extending along a longitudinal axis;

rotating the bone cutting tool about the longitudinal axis while driving the bone cutting tool from the outer surface of the bone to a predetermined depth in the bone to form a bore;

slidingly engaging the body portion of the bone cutting tool with a sleeve at a first position near the proximal end of the body portion to form the bore, the sleeve having an inner diameter smaller than the second diameter;

moving the sleeve to a second position toward the distal end of the body portion and against the drilling portion;

continuously rotating the bone cutting tool at the predetermined depth to establish an enlarged bone pocket at a distal end of the bore while the sleeve is in the second position, the bone pocket defining a shoulder extending around a circumference between the bone pocket and the bore;

removing the bone cutting tool from the bone pocket and the bore;

inserting the fixation device into the bone pocket through the bore; and positioning the fixation device against the shoulder of the bone pocket.

2. The method of claim 1, wherein continuously rotating the bone cutting tool is performed without removing the bone cutting tool from the bore and after rotating the bone cutting tool into position at the predetermined depth.

3. The method of claim 1, wherein rotating the bone cutting tool further comprises:
cutting the bone with the drill tip of the bone cutting tool.

4. The method of claim 1, further comprising:
removing the bone at the distal end of the bore to form the bone pocket by the continuously rotating the bone cutting tool at the predetermined depth.

5. The method of claim 1, further comprising:
transversely cutting the bone to establish the bone pocket.

6. The method of claim 1, wherein the sleeve has an offset axis at a distance from the longitudinal axis, wherein the continuous rotation of the bone cutting tool is about the offset axis.

7. The method of claim 6, wherein the continuous rotation of the bone cutting tool is eccentric to rotation of the bone cutting tool about the longitudinal axis.

8. A method for attaching a fixation device to a bone, the method comprising:
bringing a bone cutting tool into engagement with an outer surface of the bone, the cutting tool having a body portion and a drilling portion, the body portion having a constant first diameter, a proximal end and a distal end, the drilling portion having a second diameter larger than the first diameter, the body portion extending along a first longitudinal axis;

rotating the bone cutting tool about the first longitudinal axis and relative to a sleeve having a second longitudinal axis while driving the bone cutting tool from the outer surface of the bone to a depth in the bone to form a bore while the sleeve is in a first position near the proximal end of the body portion, the sleeve having an inner diameter smaller than the second diameter;

moving the sleeve to a second position near the distal end and against the drilling portion;

rotating the bone cutting tool relative to the sleeve to form a bone pocket in the bore while the sleeve is in the second position;

removing the bone cutting tool from the bone pocket and the bore; and inserting the fixation device into the bone pocket through the bore.

9. The method of claim 8, further comprising:
forming the bone pocket in the bone to have a shoulder extending around at least a portion of a circumference between the bone pocket and the bore; and
positioning the fixation device against the shoulder of the bone pocket.

10. The method of claim 8, wherein the second longitudinal axis of the sleeve is an offset axis at a distance from the first longitudinal axis.

11. The method of claim 8, further comprising axially moving the sleeve with the bone cutting tool while driving the bone cutting tool from the outer surface of the bone to the depth in the bone to form the bore.

12. The method of claim 8, further comprising maintaining the sleeve in a proximal position relative to the body portion of the cutting tool while driving the bone cutting tool from the outer surface of the bone to the depth.

13. The method of claim 12, further comprising:
upon reaching the depth in the bone, moving the sleeve distally relative to the body portion to position at least a portion of the sleeve in the bore.

14. The method of claim 13, further comprising moving the sleeve distally until a shoulder of the sleeve engages the outer surface of the bone.

15. A method for attaching a fixation device to a bone, the method comprising:
bringing a bone cutting tool into engagement with an outer surface of the bone, the cutting tool having a body portion and a drilling portion, the body portion having a constant first diameter, a proximal end and a distal end, the drilling portion having a second diameter larger than the first diameter, the body portion extending along a longitudinal axis;

rotating the bone cutting tool about the longitudinal axis while driving the bone cutting tool from the outer surface of the bone to a depth in the bone to form a bore while a sleeve is positioned about the body portion in a first position near the proximal end of the body portion, the sleeve having an inner diameter smaller than the second diameter;

sliding the sleeve to a second position near the distal end and against the drilling portion;

rotating the bone cutting tool at the depth with the sleeve at the second position to form a bone pocket in the bore; and forming a shoulder extending around a circumference between the bone pocket and the bore.

16. The method of claim 15, further comprising:
removing the bone cutting tool from the bone pocket and the bore; and
inserting the fixation device into the bone pocket through the bore.

17. The method of claim 16, further comprising:
forming the bone pocket to include a shoulder between the bone pocket and the bore; and
positioning the fixation device against the shoulder of the bone pocket.

18. The method of claim 15, wherein the sleeve has an offset axis at a distance from the longitudinal axis, wherein rotation of the bone cutting tool is about the offset axis.

19. The method of claim 15, further comprising:
transversely cutting the bone to form the bone pocket.

* * * * *